United States Patent [19]

Hattori et al.

[11] Patent Number: 6,005,098

[45] Date of Patent: Dec. 21, 1999

[54] 5'DEOXYCYTIDINE DERIVATIVES

[75] Inventors: Kazuo Hattori, Chigasaki; Tohru Ishikawa; Hideo Ishitsuka, both of Yokohama; Yasunori Kohchi, Fujisawa; Nobuhiro Oikawa, Yokohama; Nobuo Shimma, Chigasaki; Hitomi Suda, Fujisawa, all of Japan

[73] Assignee: Hoffmann-La Roche Inc., Nutley, N.J.

[21] Appl. No.: 09/234,200

[22] Filed: Jan. 20, 1999

[30] Foreign Application Priority Data

May 7, 1998 [EP] European Pat. Off. .............. 98108321
Jun. 6, 1998 [EP] European Pat. Off. .............. 98102080

[51] Int. Cl.$^6$ ..................................................... C07H 19/06
[52] U.S. Cl. ................... 536/28.52; 536/28.1; 536/28.4; 536/28.5; 536/28.51; 536/28.54
[58] Field of Search ................... 536/28.5, 28.1, 536/28.51, 28.52, 28.54, 28.4

[56] References Cited

U.S. PATENT DOCUMENTS

| | | |
|---|---|---|
| 4,328,229 | 5/1982 | Fujii et al. . |
| 4,395,406 | 7/1983 | Gacek et al. ............................ 514/49 |
| 4,650,801 | 3/1987 | Fujii et al. . |
| 4,966,891 | 10/1990 | Fujiu et al. . |
| 5,453,497 | 9/1995 | Kamiya et al. . |
| 5,472,949 | 12/1995 | Arasaki et al. . |
| 5,525,603 | 6/1996 | Shirasaka et al. . |

FOREIGN PATENT DOCUMENTS

| | | |
|---|---|---|
| 0 882 734 | 12/1998 | European Pat. Off. . |
| 54-129131 | 6/1979 | Japan . |
| 55-5111420 | 8/1980 | Japan . |
| WO 92/01452 | 2/1992 | WIPO . |
| WO 92/04901 | 4/1992 | WIPO . |

*Primary Examiner*—James O. Wilson
*Attorney, Agent, or Firm*—George W. Johnston; Patricia S. Rocha-Tramaloni; Robert A. Silverman

[57] ABSTRACT

Compounds of the formula (I)

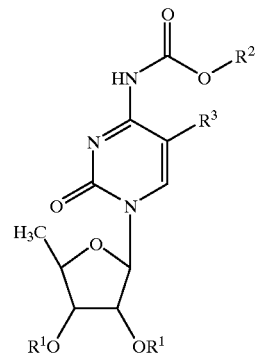

wherein $R^1$ is each independently hydrogen or a group easily hydrolyzable under physiological conditions;

$R^2$ is —$(CH_2)_n$-cycloalkyl wherein cycloalkyl contains 3 to 5 carbon atoms and n is an integer from 0 to 4, heteroaryl-(lower-alkyl), (lower-alkoxy)-(lower-alkyl), aryloxy-(lower-alkyl), aralkyloxy-(lower-alkyl), (lower-alkylthio)-(lower-alkyl), arylthio-(lower-alkyl), aralkylthio-(lower-alkyl), oxo-(lower-alkyl), acylamino-(lower-alkyl), cyclic amino-(lower-alkyl), (2-oxocyclic amino)-(lower-alkyl) wherein the alkylene chain is unsubstituted or substituted with one or two lower-alkyl group (s); and $R^3$ is iodo, or a vinyl or ethynyl group which group is unsubstituted or substituted by one or more substituents selected from the group consisting of halogen, $C_{1-4}$ alkyl, cycloalkyl, aralkyl, carbocyclic aromatic ring and heterocyclic aromatic ring.

The compounds of formula I are useful in the treatment of malignant diseases and can also be administered together with 5-fluorouracil or derivatives thereof to enhance the antitumour activity of the latter.

79 Claims, No Drawings

5'DEOXYCYTIDINE DERIVATIVES

FIELD OF THE INVENTION

The present invention is concerned with 5'-deoxycytidine derivatives, pharmaceutical compositions, a kit thereof for assisting a delivery of 5-fluorouracil selectively to tumor tissues and process for manufacturing the novel 5'-deoxycytidine derivatives.

BACKGROUND OF THE INVENTION

Although 5-fluorouracil (5-FU) or its derivatives are clinically useful antitumor agents for the treatment of various solid tumors, in general they are still not satisfactory in terms of efficacy and safety. These drawbacks are mainly due to rapid inactivation of 5-FU by dihydropyrimidine dehydrogenase (DPD) and/or the unsatisfactory delivery of 5-FU to tumor tissues with respect to tumor selectivity. Attempts to enhance the antitumor activity of 5-FU or its derivatives by inhibition of DPD have already been reported: the co-administration of 5-FU or its derivative with a DPD inhibitor such as uracil [U.S. Pat. No. 4,328,229], 5-ethynyluracil [WO92/04901], 5-chloro-2,4-dihydroxypyridine [U.S. Pat. No. 5,525,603] etc. Such co-administration resulted in enhancement of the antitumor activity of 5-FU or its derivatives, but the safety profile was not so improved due to insufficient selectivity in delivering the DPD inhibitor to tumor tissues (as a consequence, 5-FU level is increased in both tumor and plasma).

BRIEF SUMMARY OF THE INVENTION

The present invention relates to 5'-deoxy-cytidine derivatives represented by the formula (I),

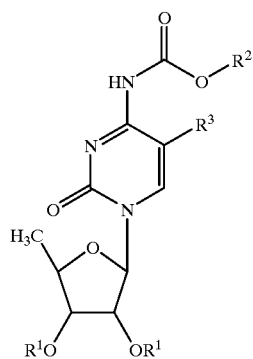

(I)

wherein $R^1$ is each independently hydrogen or a group easily hydrolyzable under physiological conditions;

$R^2$ is —$(CH_2)_n$-cycloalkyl wherein cycloalkyl contains 3 to 5 carbon atoms and n is an integer from 0 to 4, heteroaryl-(lower-alkyl), (lower-alkoxy)-(lower-alkyl), aryloxy-(lower-alkyl), aralkyloxy-(lower-alkyl), (lower-alkylthio)-(lower-alkyl), arylthio-(lower-alkyl), aralkylthio-(lower-alkyl), oxo-(lower-alkyl), acylamino-(lower-alkyl), cyclic amino-(lower-alkyl), (2-oxocyclic amino)-(lower-alkyl) wherein the alkylene chain is unsubstituted or substituted with one or two lower-alkyl group(s); and $R^3$ is iodo, or a vinyl or ethynyl group which group is unsubtituted or substituted with one or more substituents selected from the group consisting of halogen, $C_{1-4}$ alkyl, cycloalkyl, aralkyl, carbocyclic aromatic ring and heterocyclic aromatic ring.

In accordance with the present invention it has been found that the co-administration of the 5'-deoxycytidine derivatives of the formula I with 5-FU or its derivative results in a significantly improved delivery of 5-FU selectively to tumor tissues as compared with the combination of 5-FU or its derivative with a known DPD inhibitor such as 5-ethynyluracil, and shows significantly improved antitumor activity in human cancer xenograft models.

The compounds of formula I are also useful for the treatment of malignant diseases, particularly of colorectal cancer, breast cancer, stomach cancer, lung cancer, cervical cancer or bladder cancer.

DETAILED DESCRIPTION OF THE INVENTION

The respective groups of the formula (I) are explained in more detail as follows:

The term "lower" means a carbon chain preferably containing up to and including 5 carbon atoms, unless otherwise indicated.

The term "a group easily hydrolyzable under physiological condition" preferably means acetyl, propionyl, benzoyl, toluoyl, glycyl, alanyl, b-alanyl, valyl, lysyl, and the like.

The group "—$(CH_2)_n$-cycloalkyl wherein cycloalkyl consists of 3 to 5 carbon atoms and n is an integer from 0 to 4" preferably means cyclobutyl, cyclopropylmethyl, cyclopentylmethyl and the like.

Heteroaryl-(lower-alkyl) preferably means pyridin-3-ylmethyl, pyridin-2-ylmethyl, pyridin4-ylmethyl, 1-(pyridin4-yl)ethyl, (6-methylpyridin-2-yl)methyl, 1-(6-methylpyridin-2-yl)propyl and the like.

(Lower-alkoxy)-(lower-alkyl) preferably means 2-methoxy-ethyl, 2-ethoxyethyl, 3-methoxypropyl, 3-ethoxypropyl, 3-methoxy-3-methylbutyl, 3-ethoxy-3-methylbutyl, 3-methoxy-2,2-dimethylpropyl, 3-ethoxy-2,2-dimethylpropyl, 2-ethyl-2-methoxymethylbutyl, 2-ethyl-2-ethoxymethylbutyl and the like.

Aryloxy-(lower-alkyl) preferably means 2-phenoxyethyl, 1-phenoxypropyl, 3-phenoxypropyl and the like.

Aralkyloxy-(lower-alkyl) preferably means 2-benzyloxyethyl, 3-benzyloxypropyl, 5-benzyloxypenty and the like.

(Lower-alkylthio)-(lower-alkyl) preferably means 2-methylthioethyl, 2-ethylthioethyl, 3-methylthiopropyl, 3-ethylthiopropyl and the like.

Arylthio-(lower-alkyl) preferably means 2-phenylthioethyl, 3-phenylthiopropyl and the like.

Aralkylthio-(lower-alkyl) preferably means 2-(benzylthio)ethyl, 3-(benzylthio)propyl and the like.

Oxo-(lower-alkyl)-preferably means 4-oxopentyl, 3-oxo-2-methylbutyl, 2-oxobutyl and the like.

Acylamino-(lower-alkyl) preferably means 2-(acetylamino)-ethoxy, 3-(acetylamino)propyl, 3-(n-propionylamino)propyl, 3-(benzoylamino)propyl and the like.

Cyclic amino-(lower-alkyl) preferably means 2-morpholinoethyl, 3-morpholinopropyl, 2-piperidinoethyl, 3-piperidinopropyl, 2-pyrrolidinoethyl, 3-pyrrolidinopropyl and the like.

(2-Oxocyclic amino)-(lower-alkyl) preferably means 2-oxopyrrolidin-1-ylethyl, 2-oxopiperidin-1-ylethyl and the like.

The term "a vinyl or ethynyl group which group is unsubstituted or substituted with one or more substsituents selected from the group consisting of halogen, $C_{1-4}$ alkyl, cycloalkyl, aralkyl, carbocyclic aromatic ring and heterocyclic aromatic ring" preferably means vinyl, 1-chlorovinyl, 2-bromovinyl, 2-bromo-1-chlorovinyl, 2-phenylvinyl, ethynyl, prop-1-ynyl, but-1-ynyl, pent-1-ynyl, hex-1-ynyl, 3,3-dimethyl-but-1-ynyl, cyclopentylethynyl, cyclohexylethynyl, phenylethynyl, 3-phenylprop-1-ynyl, pyrid-2-ylethynyl, imidazol-2-ylethynyl, and the like. Most preferred are vinyl and ethynyl.

Preferred groups $R^2$ are (lower-alkoxy)-(lower-alkyl) groups.

Preferred 5-ethynyl-5'-deoxycytidine derivatives of the present invention are:

5'-deoxy-5-ethynyl-$N^4$-[(2-methoxyethoxy)carbonyl]cytidine,

5'-deoxy-5-ethynyl-$N^4$-[(3-methoxy-3-methylbutoxy)carbonyl]-cytidine,

5'-deoxy-5-ethynyl-$N^4$-[(3-ethoxypropoxy)carbonyl]cytidine,

5'-deoxy-5-ethynyl-$N^4$-[(3-methoxy-2,2-dimethylpropoxy)-carbonyl]cytidine,

5'-deoxy-5-ethynyl-$N^4$-[[2-ethyl-2-(methoxymethyl)butoxy]-carbonyl]cytidine,

5'-deoxy-5-ethynyl-$N^4$-[(3-benzyloxypropoxy)carbonyl]cytidine,

5'-deoxy-5-ethynyl-$N^4$-(cyclobutoxycarbonyl)cytidine,

5'-deoxy-5-ethynyl-$N^4$-[(cyclopropylmethoxy)carbonyl]cytidine,

5'-deoxy-5-ethynyl-$N^4$-[(cyclobutylmethoxy)carbonyl]cytidine,

5'-deoxy-5-ethynyl-$N^4$-[(cyclopentylmethoxy)carbonyl]cytidine,

5'-deoxy-5-ethynyl-$N^4$-[(2-methylthioethoxy)carbonyl]cytidine,

5'-deoxy-5-ethynyl-$N^4$-[(2-ethylthioethoxy)carbonyl]cytidine,

5'-deoxy-5-ethynyl-$N^4$-[(2-phenylthioethoxy)carbonyl]cytidine,

5'-deoxy-5-ethynyl-$N^4$-[(2- methylthiopropoxy)carbonyl]cytidine,

5'-deoxy-5-ethynyl-$N^4$-[(4-oxopentyloxy)carbonyl]cytidine,

5'-deoxy-5-ethynyl-$N^4$-[[2-(2-oxopyrrolidin-1-yl)ethoxy]-carbonyl]cytidine,

5'-deoxy-5-ethynyl-$N^4$-[[3-(acetylamino)propoxy]carbonyl]-cytidine,

5'-deoxy-5-ethynyl-$N^4$-[[3-(n-propionylamino)propoxy]-carbonyl]cytidine,

5'-deoxy-5-ethynyl-$N^4$-[(2-morpholinoethoxy)carbonyl]cytidine,

5'-deoxy-5-ethynyl-$N^4$-[(pyridin-3-ylmethoxy)carbonyl]cytidine,

2',3'-di-O-acetyl-5'-deoxy-5-ethynyl-$N^4$-[(3-methoxy-3-methylbutoxy)-carbonyl]cytidine, and the like.

Preferred 5'-deoxy-5-iodocytidine derivatives of the present invention are:

5'-deoxy-5-iodo-$N^4$-[(2-methoxyethoxy)carbonyl]cytidine,

5'-deoxy-5-iodo-$N^4$-[(3-methoxy-3-methylbutoxy)carbonyl]-cytidine,

5'-deoxy-$N^4$-[(3-ethoxypropoxy)carbonyl]-5-iodocytidine,

5'-deoxy-5-iodo-$N^4$-[(3-methoxy-2,2-dimethylpropoxy)-carbonyl]cytidine,

5'-deoxy-$N^4$-[[2-ethyl-2-(methoxymethyl)butoxy]carbonyl]-5-iodocytidine,

5'-deoxy-$N^4$-[(3-benzyloxypropoxy)carbonyl]-5-iodocytidine,

5'-deoxy-$N^4$-(cyclobutoxycarbonyl)-5-iodocytidine,

5'-deoxy-$N^4$-[(cyclopentylmethoxy)carbonyl]-5-iodocytidine,

5'-deoxy-$N^4$-[(cyclobutylmethoxy)carbonyl]-5-iodocytidine,

5'-deoxy-$N^4$-[(cyclopentylmethoxy)carbonyl]-5-iodocytidine,

5'-deoxy-$N^4$-[(2-methylthioethoxy)carbonyl]-5-iodocytidine,

5'-deoxy-5-iodo-$N^4$-[(2-ethylthioethoxy)carbonyl]cytidine,

5'-deoxy-$N^4$-[(2-phenylthioethoxy)carbonyl]-5-iodocytidine,

5'-deoxy-5-iodo-$N^4$-[(2-methylthiopropoxy)carbonyl]cytidine,

5'-deoxy-5-iodo-$N^4$-[(4-oxopentyloxy)carbonyl]cytidine,

5'-deoxy-5-iodo-$N^4$-[[2-(2-oxopyrrolidin-1-yl)ethoxy]-carbonyl]cytidine, $N^4$-[[3-(acetylamino)propoxy]carbonyl]-5'-deoxy-5-iodocytidine, 5'-deoxy-5-iodo-$N^4$-[[3-(n-propionylamino)propoxy]-carbonyl]cytidine, 5'-deoxy-5-iodo-$N^4$-[(2-morpholinoethoxy)carbonyl]cytidine, 5'-deoxy-5-iodo-$N^4$-[(pyridin-3-ylmethoxy)carbonyl]cytidine, 2',3'-di-O-acetyl-5'-deoxy-5-iodo-$N^4$-[(3-methoxy-3-methylbutoxy)-carbonyl]cytidine and the like.

Preferred 5'-deoxy-5-vinylcytidine derivatives of the present invention are:

5'-deoxy-$N^4$-[(2-methoxyethoxy)carbonyl]-5-vinylcytidine,

5'-deoxy-$N^4$-[(3-methoxy-3-methylbutoxy )carbonyl]-5-vinyl -cytidine,

5'-deoxy-$N^4$[(3-ethoxypropoxy)carbonyl]-5-vinylcytidine,

5'-deoxy-$N^4$-[(3-methoxy-2,2-dimethylpropoxy)carbonyl]-5-vinylcytidine,

5'-deoxy-$N^4$-[[2-ethyl-2-(methoxymethyl)butoxy]carbonyl]-5-vinylcytidine, $N^4$-[(3-benzyloxypropoxy)carbonyl]-5'-deoxy-5-vinylcytidine, $N^4$-(cyclobutoxycarbonyl)-5'-deoxy-5-vinylcytidine, $N^4$-[(cyclopropylmethoxy)carbonyl]-5'-deoxy-5-vinylcytidine, $N^4$-[(cyclobutylmethoxy)carbonyl]-5'-deoxy-5-vinylcytidine, $N^4$-[(cyclopentylmethoxy)carbonyl]-5'-deoxy-5-vinylcytidine, 5'-deoxy-$N^4$-[(2-methylthioethoxy)carbonyl]-5-vinylcytidine, 5'-deoxy-$N^4$-[(2-ethylthioethoxy)carbonyl]-5-vinylcytidine, 5'-deoxy-$N^4$-[(2-phenylthioethoxy)carbonyl]-5-vinylcytidine, 5'-deoxy-N⁴-[(2-methylthiopropoxy)carbonyl]-5-vinylcytidine,
5'-deoxy-N⁴-[(4-oxopentyloxy)carbonyl]-5-vinylcytidine,
5'-deoxy-N⁴-[[2-(2-oxopyrrolidin-1-yl)ethoxy]carbonyl]-5-vinylcytidine,
N⁴-[[3-(acetylamino)propoxy]carbonyl]-5'-deoxy-5-vinylcytidine,
5'-deoxy-N⁴-[[3-(n-propionylamino)propoxy]-5-vinylcytidine,
5'-deoxy-N⁴-[(2-morpholinoethoxy)carbonyl]-5-vinylcytidine,
5'-deoxy-N⁴-[(pyridin-3-ylmethoxy)carbonyl]-5-vinylcytidine,
2',3'-di-O-acetyl-5'-deoxy-N⁴-[(3-methoxy-3-methylbutoxy)carbonyl]-5-vinylcytidine, and the like.

The 5'-deoxycytidine derivatives represented by the formula (I) can be produced according to the following methods. In the following process A-D, P¹ represents a hydroxy protecting group such as acetyl, benzoyl, trimethylsilyl, tert-butyldimethylsilyl and the like.

Process A: A compound represented by the formula (II),

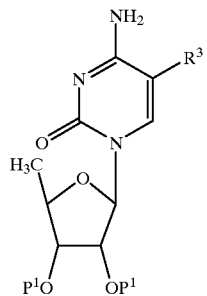

(II)

wherein P¹ is a hydroxy-protecting group, and R³ is the same as defined above, is reacted with a compound represented by the general formula (III),

R²OCOX    (III)

wherein R² is as defined above; X is chloro or bromo, in the presence of acid acceptor, followed, if necessary, by removal of protecting group(s).

Process B: A compound represented by the formula (IV)

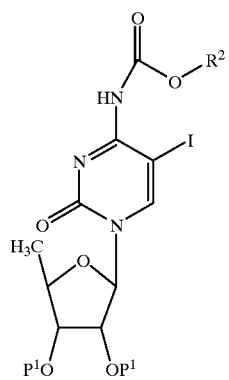

(IV)

wherein P¹ and R² are as defined above, is reacted with an acetylene or vinyl derivative in the presence of a palladium catalyst, followed, if necessary, by removal of protecting group(s).

Process C: A compound represented by the formula (V)

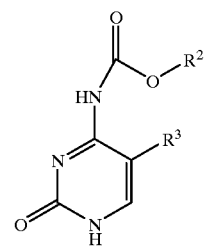

(V)

wherein R² and R³ are as defined above, is coupled with a compound represented by the formula (VI)

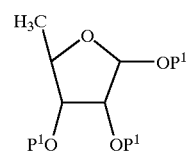

(VI)

wherein P¹ is as defined above, in the presence of Lewis acid catalyst, followed, if necessary, by removal of protecting group(s).

Process D:

Compounds represented by the formula (I) wherein R³ is a vinyl group which is unsubstituted or substituted with one or more substituents selected from the group consisting of halogen, $C_{1-4}$ alkyl, cycloalkyl, aralkyl, carbocyclic aromatic ring and heterocyclic aromatic ring, R¹ and R² are as defined above can be prepared by catalytic hydrogenation of a compound represented by the formula (VII)

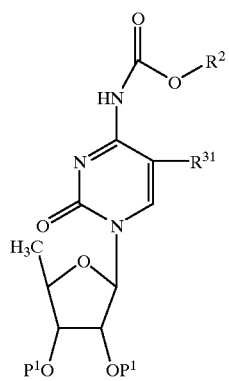

(VII)

wherein R³¹ is an ethynyl group which is unsubstituted or substituted with one or more substituents selected from the group consisting of halogen atom(s), $C_{1-4}$ alkyl, cycloalkyl, aralkyl, or aromatic ring which may have one or more hetero atom(s)), and R² and P¹ as defined above, with a Lindlar catalyst, followed, if necessary, by removal of protecting group(s).

Process A:

Specific examples of the compound represented by the formula (II) include
2',3'-di-O-acetyl-5'-deoxy-5-ethynylcytidine,
2',3'-bis-O-(tert-butyldimethylsilyl)-5'-deoxy-5-ethynylcytidine, 2',3'-di-O-acetyl-5'-deoxy-5-prop-1-ynylcytidine,
2',3'-bis-O-(tert-butyldimethylsilyl)-5'-deoxy-5-prop-1-ynylcytidine,
2',3'-di-O-acetyl-5-but-1-ynyl-5'-deoxycytidine,
2',3'-bis-O-(tert-butyidimethylsilyl)-5-but-1-ynyl-5'-deoxycytidine,
2',3'-di-O-acetyl-5'-deoxy-5-pent-1-ynylcytidine,
2',3'-bis-O-(tert-butyldimethylsilyl)-5'-deoxy-5-pent-1-ynylcytidine,
2',3'-di-O-acetyl-5'-deoxy-5-hex-1-ynylcytidine,
2',3'-bis-O-(tert-butyldimethylsilyl)-5'-deoxy-5-hex-1-ynylcytidine,
2',3'-di-O-acetyl-5'-deoxy-5-iodocytidine,
2',3'-bis-O-(tert-butyldimethylsilyl)-5'-deoxy-5-iodocytidine,
2',3'-di-O-acetyl-5-(1-chlorovinyl)-5'-deoxycytidine,
2',3'-bis-O-(tert-butyldimethylsilyl)-5-(1-chlorovinyl)-5'-deoxycytidine,
2',3'-di-O-acetyl-5'-deoxy-5-vinylcytidine,
2',3'-bis-O-(tert-butyldimethylsilyl)-5'-deoxy-5-vinylcytidine, and the like.

The reaction of the compound of the above formula (II) with the compound of the above formula (III) can be carried out in a solvent such as pyridine, dioxane, tetrahydrofuran, acetonitrile, chloroform, dichloromethane and the like in the presence of an acid acceptor such as triethylamine, pyridine, picoline, 4-(N,N-dimethylamino)pyridine, lutidine and the like. The reaction can be carried out at a temperature between 0 and 30° C. The protecting group(s) may, if necessary, be removed after the reaction by the procedures known to those skilled in the art, e.g. by basic or acidic hydrolysis, or treatment with fluoride anion.

Process B:

Specific examples of the compound represented by the formula (IV) include
2',3'-bis-O-(tert-butyidimethylsilyl)-5'-deoxy-5-iodo-$N^4$-[(2-methoxy-ethoxy)carbonyl]cytidine,
2',3'-di-O-acetyl-5'-deoxy-5-iodo-$N^4$-[(3-methoxy-3-methyl-butoxy)carbonyl]-cytidine,
2',3'-di-O-acetyl-5'-deoxy-5-iodo-$N^4$-[(3-ethoxypropoxy)-carbonyl]cytidine,
2',3'-bis-O-(tert-butyldimethylsilyl)-5'-deoxy-5-iodo-$N^4$-[(3-methoxy-2,2-dimethylpropoxy)carbonyl]cytidine,
2',3'-di-O-acetyl-5'-deoxy-5-iodo-$N^4$-[(3-methoxy-2,2-dimethylpropoxy)-carbonyl]cytidine,
2',3'-di-O-acetyl-5'-deoxy-5-iodo-$N^4$-[[2-ethyl-2-(methoxy-methyl)butoxy]-carbonyl]cytidine,
2',3'-di-O-acetyl-5'-deoxy-5-iodo-$N^4$-[(3-benzyloxypropoxy)-carbonyl]cytidine,
2',3'-di-O-acetyl-5'-deoxy-5-iodo-$N^4$-(cyclobutoxycarbonyl)-cytidine,
2',3'-di-O-acetyl-5'-deoxy-5-iodo-$N^4$-[(cyclopropylmethoxy)-carbonyl]cytidine,
2',3'-di-O-acetyl-5'-deoxy-5-iodo-$N^4$-[(cyclobutylmethoxy)-carbonyl]cytidine,
2',3'-di-O-acetyl-5'-deoxy-5-iodo-$N^4$-[(cyclopentylmethoxy)-carbonyl]cytidine,
2',3'-di-O-acetyl-5'-deoxy-5-iodo-$N^4$-[(2-methylthioethoxy)-carbonyl]cytidine,
2',3'-di-O-acetyl-5'-deoxy-5-iodo-$N^4$-[(2-ethylthioethoxy)-carbonyl]cytidine,
2',3'-di-O-acetyl-5'-deoxy-5-iodo-$N^4$-[(2-phenylthioethoxy)-carbonyl]cytidine,
2',3'-di-O-acetyl-5'-deoxy-5-iodo-$N^4$-[(2-methylthiopropoxy)-carbonyl]cytidine,
2',3'-di-O-acetyl-5'-deoxy-5-iodo-$N^4$-[(4-o xopentyloxy)-carbonyl]cytidine,
2',3'-di-O-acetyl-5'-deoxy-5-iodo-$N^4$-[[2-(2-oxopyrrilidin-1-yl)ethoxy]-carbonyl]cytidine,
2',3'-di-O-acetyl-5'-deoxy-5-iodo-$N^4$-[[3-(acetylamino)-propoxy]carbonyl]cytidine,
2',3'-di-O-acetyl-5'-deoxy-5-iodo-$N^4$-[[3-(n-propionylamino)-propoxy]carbonyl]-cytidine,
2',3'-di-O-acetyl-5'-deoxy-5-iodo-$N^4$-[(2-morpholinoethoxy)-carbonyl]cytidine,
2',3'-di-O-acetyl-5'-deoxy-5-iodo-$N^4$-[(pyridin-3-ylmethoxy)-carbonyl]cytidine, and the like.

The specific examples of the acetylene or vinyl derivatives used for this coupling reaction are trimethysilyl acetylene, tert-butyldimethysilyl acetylene, 1-butyne, 1-pentyne, 1-heptyne, 1-hexyne, 3-methyl-1-butyne, 3,3-dimethyl-1-butyne, cyclohexylacetylene, phenylacetylene, 3-phenyl-1-propyne, tri-n-butyl(vinyl)stannane and the like.

The coupling reaction of a compound represented by the formula (IV) with an acetylene derivative can be performed with a palladium catalyst such as bis(triphenylphosphine) palladium (II) chloride-copper (I) iodide, bis (triphenylphosphine)palladium(II) acetate-copper(I) iodide and the like. The coupling reaction of a compound represented by the formula (IV) with a vinyl derivative can be performed in the presence of a palladium catalyst such as tris(dibenzylideneacetone)-dipalladium (0) ($Pd_2(dba)_3$), tetrakis(triphenylphosphine)-palladium (0), bis(acetonitrile) palladium(II) chloride in the presence of tri-2-furylphosphine, triphenylphosphine and the like.

These reaction can be carried out in a solvent such as chloroform, dichloromethane, tetrahydrofurane, N-methylpyrrolidone, N,N-dimethyformamide and the like. The reaction can be carried out at a temperature between 0 and 80° C., preferably between 10 and 60° C.

Process C:

Specific examples of the compounds represented by the formula (V) include
5-ethynyl-$N^4$-[(2-methoxyethoxy)carbonyl]cytosine,
5-ethynyl-$N^4$-[(3-methoxy-3-methylbutoxy)carbonyl]cytosine,
5-ethynyl-$N^4$-[(3-ethoxypropoxy)carbonyl]cytosine,
5-ethynyl-$N^4$-[(3-methoxy-2,2-dimethylpropoxy)carbonyl]cytosine,
5-ethynyl-$N^4$-[[2-ethyl-2-(methoxymethyl)butoxy]-carbonyl]cytosine,
5-ethynyl-$N^4$-[(3-benzyloxypropoxy)carbonyl]cytosine,
5-ethynyl-$N^4$-(cyclobutoxycarbonyl)cytosine,
5-ethynyl-$N^4$-[(cyclopropylmethoxy)carbonyl]cytosine,
5-ethynyl-$N^4$-[(cyclobutylmethoxy)carbonyl]cytosine,
5-ethynyl-$N^4$-[(cyclopentylmethoxy)carbonyl]cytosine,
5-ethynyl-$N^4$-[(2-methylthioethoxy)carbonyl]cytosine,
5-ethynyl-$N^4$-[(2-ethylthioethoxy)carbonyl]cytosine,
5-ethynyl-$N^4$-[(2-phenylthioethoxy)carbonyl]cytosine,
5-ethynyl-$N^4$-[(2-methylsulfanylpropoxy)carbonyl]cytosine,
5-ethynyl-$N^4$-[(4-oxopentyloxy)carbonyl]cytosine,
5-ethynyl-$N^4$-[[2-(2-oxopyrrilidin-1-yl)ethoxy]-carbonyl]cytosine,
5-ethynyl-$N^4$-[[3-(acetylamino)propoxy]carbonyl]cytosine, 5-ethynyl-$N^4$-[[3-(n-propionylamino)propoxy]-carbonyl]cytosine, 5-ethynyl-$N^4$-[(2-morpholinoethoxy)carbonyl]cytosine, 5-ethynyl-$N^4$-[(pyridin-3-ylmethoxy)carbonyl]cytosine, $N^4$-[(3-methoxy-2,2-dimethylpropoxy)carbonyl]-5-vinylcytosine, and the like.

Specific examples of the compound represented by the formula (VI) include 5-deoxy-1,2,3-tri-O-acetyl-D-ribofuranoside 5-deoxy-1,2,3-tri-O-benzoyl-D-ribofuranoside, and the like.

A compound of the formula (V) may be first converted to the trimethylsilyl derivative with silylation reagent such as hexamethyldisilazane, followed by the coupling reaction with a compound represented by the formula (VI) in the presence of Lewis acid catalyst such as tin(IV) chloride, titanium(IV) chloride and the like. This coupling reaction proceeds in a solvent such as acetonitrile, dichloromethane, chloroform, 1,2-dichloroethane, nitromethane, toluene and the like, at a temperature between 0 and 30° C., preferably between 0 and 10° C.

Process D:

Specific examples of the compounds represented by the formula (VII) include

5'-deoxy-5-ethynyl-$N^4$-[(2-methoxyethoxy)carbonyl]cytidine,

5'-deoxy-5-ethynyl-$N^4$-[(3-methoxy-3-methylbutoxy)carbonyl]-cytidine,

5'-deoxy-5-ethynyl-$N^4$-[(3-ethoxypropoxy)carbonyl]cytidine,

5'-deoxy-5-ethynyl-$N^4$-[(3-methoxy-2,2-dimethylpropoxy)-carbonyl]cytidine,

5'-deoxy-5-ethynyl-$N^4$-[[2-ethyl-2-(methoxymethyl)butoxy]-carbonyl]cytidine,

5'-deoxy-5-ethynyl-$N^4$-[(3-benzyloxypropoxy)carbonyl]cytidine,

5'-deoxy-5-ethynyl-$N^4$-(cyclobutoxy]carbonyl)cytidine,

5'-deoxy-5-ethynyl-$N^4$-[(cyclopropylmethoxy)carbonyl]cytidine,

5'-deoxy-5-ethynyl-$N^4$-[(cyclobutylmethoxy)carbonyl]cytidine,

5'-deoxy-5-ethynyl-$N^4$-[(cyclopentylmethoxy)carbonyl]cytidine,

5'-deoxy-5-ethynyl-$N^4$-[(2-methylthioethoxy)carbonyl]cytidine,

5'-deoxy-5-ethynyl-$N^4$-[(2-ethylthioethoxy)carbonyl]cytidine,

5'-deoxy-5-ethynyl-$N^4$-[(2-phenylthioethoxy)carbonyl]cytidine,

5'-deoxy-5-ethynyl-$N^4$-[(2-methylthiopropoxy)carbonyl]cytidine,

5'-deoxy-5-ethynyl-$N^4$-[(4-oxopentyloxy)carbonyl]cytidine,

5'-deoxy-5-ethynyl-$N^4$-[[2-(2-oxopyrrolidin-1-yl)ethoxy]-carbonyl]cytidine,

5'-deoxy-5-ethynyl-$N^4$-[[3-(acetylamino)propoxy]carbonyl]-cytidine,

5'-deoxy-5-ethynyl-$N^4$-[[3-(n-propionylamino)propoxy]-carbonyl]cytidine,

5'-deoxy-5-ethynyl-$N^4$-[(2-morpholinoethoxy)carbonyl]cytidine,

5'-deoxy-5-ethynyl-$N^4$-[(pyridin-3-ylmethoxy)carbonyl]cytidine,

2',3'-di-O-acetyl-5'-deoxy-5-ethynyl-$N^4$-[(3-methoxy-3-methylbutoxy)-carbonyl]cytidine, and the like.

The catalytic hydrogenation of the ethynyl group of the compound of formula (VII) can be performed using a Lindlar catalyst according to methods known to those skilled in the art [cf. Synthetic Method, 1952, vol. 7, p.38 (Interscience Publishers, Inc., New York)].

The compounds of formulas II–VII are all known or can be prepared by known methods from known starting materials.

The 5'-deoxycytidine derivatives of the present invention can be used as an antitumor agent together with known physiologically acceptable pharmaceutical carriers. According to a preferred aspect the present invention provides a pharmaceutical composition comprising a 5'-deoxy-cytidine derivative represented by the formula (I) and 5-FU or its derivative. With this composition, the 5'-deoxy-cytidine derivative potentiates the antitumor effect of 5-fluorouracil or its derivative by delivering significantly higher amount of 5-FU selectively to tumor tissues without significant increase of 5-FU concentration in plasma.

For the effective combination of the 5'-deoxycytidine derivative represented by the formula (I) with 5-FU or its derivative for the treatment of cancer with an improved efficacy and safety profile, a 5-FU derivative can be selected from the group consisting of:

5-fluoro-1-(2-tetrahydrofuryl)uracil, 1-(n-hexyloxycarbonyl)-5-fluorouracil,

5'-deoxy-5-fluorouridine,

5'-deoxy-5-fluoro-$N^4$-(n-propoxycarbonyl)cytidine, $N^4$-(n-butoxycarbonyl)-5'-deoxy-5-fluorocytidine, 5'-deoxy-5-fluoro-$N^4$-(n-pentyloxycarbonyl)cytidine, 5'-deoxy-5-fluoro-$N^4$-(isopentyloxycarbonyl)cytidine, 5'-deoxy-5-fluoro-$N^4$-(n-hexyloxycarbonyl)cytidine, 5'-deoxy-$N^4$-[(2-ethylbutyl)oxycarbonyl]-5-fluorocytidine, 5'-deoxy-5-fluoro-$N^4$-[(2-phenylethoxy)carbonyl]cytidine, $N^4$-[(cyclohexylmethoxy)carbonyl]-5'-deoxy-5-fluorocytidine, 5'-deoxy-5-fluoro-$N^4$-(neopentyloxycarbonyl)cytidine, 5'-deoxy-$N^4$-[(3,3-dimethylbutoxy)carbonyl]-5-fluorocytidine, 5'-deoxy-5-fluoro-$N^4$-(3,5-dimethylbenzoyl)cytidine, 5'-deoxy-5-fluoro-$N^4$-(3,5-dichlorobenzoyl)cytidine, 2',3'-di-O-acetyl-5'-deoxy-5-fluoro-$N^4$-(n-pentyloxycarbonyl)cytidine, and the like.

A pharmaceutical composition of the present invention can be obtained by formulating a compound of the formula (I) and 5-FU or its derivative into a single preparation or into two respective separate preparations.

A compound of the formula (I) in an optimal dosage form can be administered either independently or simultaneously with 5-FU or its derivative which is formulated in an optimal dosage form.

A pharmaceutical composition of the formula (I) can be administered at any time before or simultaneously with the administration of 5-FU or its derivative; preferably, within 3 hour before or simultaneously with the administration of 5-FU or its derivative.

In the pharmaceutical composition of the present invention comprising 5-FU or its derivative and a 5'-deoxycytidine derivative represented by the general formula (I), the suitable molar ratio of two components is about 0.001–10 moles, preferably 0.002–0.5 mole of a compound of the formula (I) per mole of 5-FU or its derivative.

The present invention also provides a kit comprising a component A containing an effective amount of a compound of the formula (I) and a component B containing an effective amount of 5-FU or its derivative. In the kits of the present invention, the components may be administered simultaneously or at any time before the administration of the other one; preferably, the components can be administered simultaneouly, or the pharmaceutical composition of a compound of the formula (I) may be administered within 3 hour before the administration of the pharmaceutical composition of 5-FU or its derivative.

Thus, the present invention is also concerned with the pharmaceutical compositions of-5-FU or its derivative and a kit thereof for the treatment of malignant diseases, particularly of colorectal cancer, breast cancer, stomach cancer, lung cancer, cervical cancer or bladder cancer.

The pharmaceutical compositions and the components A and B of the kit of the present invention can be administered in any form, for example, tablets, pills, suppositories, capsules, granules, powders, or emulsions etc. Pharmaceutically acceptable carriers and excipients useful in formulating the pharmaceutical composition of the present invention are those commonly used. Pharmaceutically acceptable materials can be an organic or inorganic inert carrier material suitable for enteral, percutaneous or parenteral administration such as water, gelatine, gum arabic, lactose, starch, magnesium stearate, talc, vegetable oils, polyalkylene glycols and petroleum jelly. The pharmaceutical composition provided by the present invention can be administered orally, e.g. in form of tablets, capsules, pills, powders, granules, solutions, syrups, suspensions or elixirs. The administration can also be carried out parenterally, e.g. in form of sterile solutions, suspensions or emulsions; or locally, e.g. in form of solutions, suspensions, salves, powders or aerosols. The pharmaceutical composition can be sterilized and/or can contain further adjuvants such as preserving, stabilizing setting, emulsifying agents, flavor-improving, salts for variation of the osmotic pressure or substances acting as buffers. The pharmaceutical composition can be prepared in a conventional manner.

Dosage ranges for the pharmaceutical composition of the present invention can depend on the route of administration, the age, weight and condition of the patient and the particular disease to be treated. In the case of oral, rectal or parenteral administration for adults, an approximate range from about 1 mg/body/day to about 2,000 mg/body/day of a compound of formula (I) and about 10 mg/body/day to about 4,000 mg/body/day of 5-FU or its derivative, depending on the kind of 5-FU derivative used. Oral administration is a preferred route of administration of the pharmaceutical composition according to the present invention.

The following Examples are intended to illustrate the present invention in more detail, but are not intended to limit its scope in any manner.

Reference Example 1

Preparation of 2',3'-di-O-acetyl-5'-deoxy-5-iodocytidine

5-Iodocytosine (1.0 g; 4.22 mmol) and catalytic amount of $(NH_4)_2SO_4$ were suspended in a solution of toluene (10 ml) and hexamethyidisilazane (20 ml). The suspension was heated at 110° C. for 18 hours to become a clear solution. After concentrating the reaction solution under reduced pressure, acetonitrile (25 ml) and 5-deoxy-1,2,3-tri-O-acetyl-D-ribofuranoside (1.32 g; 5.06 mmol) were added to the residue. Then, anhydrous stannic chloride(0.58 ml; 5.06 mmol) in nitromethane (5 ml) was added dropwise to the mixture over 5 minutes. During the addition, the mixture was kept below 0° C. by ice cooling. After stirring the mixture at 0~5° C. for 2 hours, 2 g of sodium bicarbonate was added followed by dropwise addition of water (0.7 ml). After the addition, the mixture was stirred vigorously at room temperature for 30 minutes. The reaction mixture was filtered to remove insoluble material, which was washed with $CH_2Cl_2$. The filtrate and washing were combined, washed with water and sat.aq. sodium bicarbonate, and then dried over $Na_2SO_4$ and filtered. The filtrate was evaporated under reduced pressure. The crude product was purified by flash chromatography on $SiO_2$ (eluent: 5% MeOH/$CH_2Cl_2$) to give 5'-deoxy-2',3'-di-O-acetyl-5-iodocytidine as a colorless solid. (1.22 g, 66% yield)

FAB-MS: (m/z) 438[M+H]$^+$, 460[M+Na]$^+$1H-NMR: (270 MHz;DMSO-d6): d 1.32 (3H, d, J=6.3), 2.04 (3H, s), 2.06 (3H, s), 4.02 (1H, quin., J=6.3), 5.14 (1H, t, J6.6), 5.48 (1H, dd, J=6.6,4.3), 5.69 (1H, d, J=4.0), 6.78 (1H, br.s), 8.01 (1H, br.s), 8.11 (1H, s)

Reference Example 2

Preparation of 2',3'-di-O-acetyl-5'-deoxy-5-[2-(trimethysilyl)-ethynyl]cytidine

To a stirred solution of 5'-deoxy-2',3'-di-O-acetyl-5-iodocytidine (1.35 g, 3.087 mmol) in $CH_2Cl_2$ (15 ml) there was added N,N-diisopropylethylamine (0.537 ml, 3.087 mmol), CuI (58 mg, 0.309 mmol), Pd(PPh$_3$)$_2$Cl$_2$ (60 mg, 0.085 mmol), and trimethylsilyl-acetylene (0.523 ml, 3.704 mmol) at room temperature under Ar. The reaction mixture was then heated to 60° C. After stirring for 2 hours, the mixture was cooled to room temperature. The solvent was removed under reduced pressure, and the residue dissolved in EtOAc (200 ml), washed with 2% aq. EDTA.2Na, water and brine, dried over $Na_2SO_4$ and filtered. The filtrate was evaporated under reduced pressure. The crude product was purified by flash chromatography on $SiO_2$ (f2.2×25 cm, eluent: EtOAc) to give 2',3'-di-O-acetyl-5'-deoxy-5-[2-(trimethylsilyl)ethynyl]cytidine as a pale yellow solid. (1.20 g, 95% y.).

FAB-MS: (m/z) 408 [M+H]$^+$, $^1$H-NMR: (270 MHz; DMSO-d$_6$): d 0.23 (9H, s), 1.34 (3H, d, J=6.3Hz), 2.05(3H, s ), 2.07 (3H, s), 4.05 (1H, quin., J=6.3 Hz ), 5.13 (1H, dd, J=6.9, 6.6), 5.48 (1H, t, J=6.6 Hz ), 5.75 (1 H, d, J=4.3 Hz), 6.83 (1H, br.s), 7.99 (1H, br.s ), 8.13 (1H, s)

Reference Example 3

Preparation of 2',3'-di-O-acetyl-5'-deoxy-5-vinylcytidine

To a solution of 2',3'-di-O-acetyl-5'-deoxy-5-iodocytidine, (1.6 g, 3.66 mmol) in 10 ml DMF were added Pd$_2$(dba)$_3$ (67 mg, 0.073 mmol) and tri-2-furylphosphine (85 mg, 0.366 mmol) and tri-n-butyl(vinyl)stannane (2.1 ml, 7.318 mmol) under Ar atmosphere at room temperature. After stirring for 19 h, tri-n-butyl(vinyl)stannane (2.1 ml, 7.318 mmol ) was added to the reaction mixture, which was then warmed up to 40° C. with stirring for 24 hours. The solvent was removed in vacuo, and the residue purified by silica gel column chromatography (eluent: ethyl acetate~$CH_2Cl_2$: MeOH=95: 5) to give 2',3'-di-O-acetyl-5'-deoxy-5-vinylcytidine (1.13 g, 92%) as a colorless solid:

FAB-MS: (m/z) 338 [M+H]$^+$, $^1$H-NMR: (270 MHz; DMSO-d6: d 1.33 (3H, d, J=6.3), 2.05 (3H, s), 2.06 (3H, s), 4.05 (1H, quin., J=6.3), 5.14 (1H, d, J=10.8),5.16 (1H, t, J=6.6),5.54(1H, d, J=17.2 ), 5.53 (1H, dd, J=6.9, 5.9 ), 5.73 (1H, d, J=4.3 ), 6.55 ( 1H, dd, J=17.2, 10.8),7.20(1H, br. s),7.57 (1H, br. s), 7.88(1H, s)

Example 1

Preparation of 5'-deoxy-5-ethynyl-N$^4$-[(3-methoxy-2,2-dimethylpropoxy)-carbonyl]cytidine a) To a solution of 2',3'-di-O-acetyl-5'-deoxy-5-[2-(trimethylsilyl)-ethynyl]cytidine (100 mg, 0.25 mmol) and triphosgene (73 mg, 0.25 mmol) in dry dichloromethane (3 ml) there was added a solution of 3-methoxy-2,2-dimethylpropanol (77 mg, 0.65 mmol) [ref. Tetrahedron Asymmetry,1995,6, 271–282] and diisopropylethylamine (182 ml,1.3 mmol) in dry dichloromethane (2 ml). After stirring for 30 min at room temperature under Ar, methanol (0.5 ml) and water (0.5 ml) were added dropwise to the reaction mixture at room temperature. After stirring for an additional 5 minutes, the reaction mixture was partitioned between dichloromethane and water. The aqueous layer was extracted with dichloromethane. The combined organic layers were washed with brine, dried over anhydrous MgSO$_4$ and filtered. The filtrate was evaporated under reduced pressure. Purification of the residue by preparative thin layer chromatography on silica gel (using n-hexane:ethyl acetate= 1:1 as a developing solvent) gave 2',3'-di-O-acetyl-5'-deoxy-N$^4$-[(3-methoxy-2,2-dimethylpropoxy)carbonyl]-5-[2-(trimethylsilyl)ethynyl]-cytidine (107 mg,79%).

b) 2',3'-di-O-acetyl-5'-deoxy-N$^4$-[(3-methoxy-2,2-dimethylpropoxy)carbonyl]-5-[2-(trimethylsilyl)ethynyl]-cytidine (100 mg, 0.18 mmol) was dissolved in methanol (4 ml), followed by addition of K$_2$CO$_3$ (38 mg,0.27 mmol). After stirring for 30 min at room temperature, the reaction mixture was evaporated under reduced pressure. Purification of the residue by preparative thin layer chlomatography on silica gel (using dichloromethane:methanol=20:1 as a developing solvent) gave 5'-deoxy-5- ethynyl-N$^4$-[(3-methoxy-2, 2-dimethylpropoxy)carbonyl]cytidine (43 mg, 60%).

FAB-MS: (m/z) 396 [M+H]$^+$, $^1$H-NMR: (270 MHz; DMSO-d6): d 0.90 (6H, s), 1.31 (3H, d, J=6.3), 3.13 (3H, s), 3.32 (2H, s), 3.69 (1H, m), 3.80–3.97 (3H, m), 4.13 (1H, m), 4.40 (1H, br.s), 5.05 (1H, d, J=5.9), 5.41 (1H, d, J=4.6), 5.66 (1H, d, J=3.6), 8.10 (1H, m), 9.55 (1H, br.s)

The following compounds (example 2–23) were obtained in a manner analogous to that of Example 1.

Example 2

5'-deoxy-5-ethynyl-N$^4$-(cyclobutoxycarbonyl)cytidine

FAB-MS: (m/z) 350 [M+H]$^+$, $^1$H-NMR: (270 MHz; DMSO-d6): d 1.31 (3H, d, J=5.9), 1.61 (1H, m), 1.75 (1H, m), 1.95–2.15 (2H, m), 2.22–2.38 (2H, m), 3.70 (1H, m), 3.90 (1H, m), 4.12 (1H, m), 4.24 (0.5H, br.s), 4.47 (0.5H, br.s), 4.89 (1H, m), 5.06 (1H, br.s), 5.42 (1H, br.s), 5.66 (1H, br.s), 7.90 (0.5H, br.s), 8.15 (0.5H, br.s), 9.49 (0.5H, br.s), 11.74 (0.5H, br.s)

Example 3

5'-deoxy-5-ethynyl-N$^4$-(cyclopropylmethoxycarbonyl)cytidine

FAB-MS: (m/z) 350 [M+H]$^+$, $^1$H-NMR: (270 MHz; DMSO-d6): d 0.31 (2H, m), 0.53 (2H, m), 1.15 (1H, m), 1.31 (3H, d, J=5.9), 3.70 (1H, m), 3.80–4.00 (3H, m), 4.14 (1H, m), 4.25 (0.5H, br.s), 4.46 (0.5H, br.s), 5.06 (1H, br.s), 5.41 (1 H, br.s), 5.67 (1H, br.s), 7.89 (0.5H, br.s), 8.15 (0.5H, br.s), 9.54 (0.5H, br.s), 11.69 (0.5H, br.s)

Example 4

5'-deoxy-5-ethynyl-N -(cyclobutylmethoxycarbonyl)cytidine

FAB-MS: (m/z) 364 [M+H]$^+$, $^1$H-NMR: (270 MHz; DMSO-d6): d 1.31 (3H, d, J=6.6),1.70–2.10 (6H, m), 2.61 (1H, m), 3.69 (1H, m), 3.90 (1H, m), 4.05 (2H, d, J=6.6), 4.14 (1H, m), 4.36 (1H, br.s), 5.05 (1H, d, J=5.9), 5.41 (1H, d, J=5.3), 5.66 (1H, d, J=4.0), 8.01 (1H, br.s)

Example 5

5'-deoxy-5-ethynyl-N$^4$-[(cyclopentylmethoxy)carbonyl]cytidine

FAB-MS: (m/z) 378 [M+H]$^+$, $^1$H-NMR: (270 MHz; DMSO-d6): d 1.17–1.39 (5H, m), 1.44–1.80 (6H, m), 2.19 (1H, m), 3.69 (1H, m), 3.84–4.04 (3H, m), 4.13 (1H, m), 4.25 (0.5H, br.s), 4.46 (0.5H, br.s), 5.06 (1H, br.s), 5.40 (1H, br.s), 5.66 (1H, br.s), 7.88 (0.5H, br.s), 8.15 (0.5H, br.s), 9.52 (0.5H, br.s), 11.68 (0.5H, br.s)

Example 6

5'-deoxy-5-ethynyl-N$^4$-[(2-methoxyethoxy)carbonyl]cytidine

FAB-MS: (m/z) 354 [M+H]$^+$, $^1$H-NMR: (270 MHz; DMSO-d6): d 1.31 (3H, d, J=6.3), 3.27 (3H, s), 3.56 (2H, t, J=4.6), 3.69 (1H, m), 3.89 (1H, m), 4.14 (1H, m), 4.19 (2H, t, J=4.6), 4.34 (1H, br.s), 5.05 (1H, d, J=5.9), 5.41 (1H, d, J=5.3), 5.66 (1H, d, J=4.0), 8.01 (1H, br.s)

Example 7

5'-deoxy-5-ethynyl-N$^4$-[(3-methoxy-3-methylbutoxy)carbonyl]cytidine

FAB-MS: (m/z) 396 [M+H]$^+$, $^1$H-NMR: (270 MHz; DMSO-d6): d 1.13 (6H, s), 1.30 (3H, d, J=6.3), 1.81 (2H, t, J=7.6), 3.10 (3H, s), 3.69 (1H, m), 3.90 (1H, m), 4.12 (2H, t, J=7.6), 4.13 (1H, m), 4.34 (1H, s), 5.06 (1H, br.s), 5.40 (1H, br.s), 5.66 (1H, d, J=4.0), 8.00 (1H, s)

Example 8

5'-deoxy-5-ethynyl-N$^4$-[(3-ethoxypropoxy)carbonyl]cytidine

FAB-MS: (m/z) 382 [M+H]$^+$, $^1$ H-NMR: (270 MHz; DMSO-d6): d 1.10 (3H, t, J=6.9), 1.31 (3H d, J=6.3), 1.84 (2H, tt, J=6.3, 6.3), 3.38–3.46 (4H, m), 3.69 (1 H, m), 3.90 (1 H, m), 4.07–4.20 (3H, m), 4.34 (1H, br.s), 5.05 (1H, d, J=5.9), 5.41 (1H, d, J=5.3), 5.66 (1H, d, J=3.6), 8.00 (5H, br.s))

Example 9

5'-deoxy-5-ethynyl-N$^4$-[(2-ethyl-2-methoxymethylbutoxy)carbonyl]-cytidine

FAB-MS: (m/z) 424 [M+H]$^+$, $^1$H-NMR: (270 MHz; DMSO-d6): d 0.78 (6H, t, J=7.6), 1.27 (4H, m), 1.31 (3H, d, J=6.3), 3.14 (2H, s), 3.24 (3H, s), 3.68 (1H, m), 3.85–3.98 (3H, m), 4.12 (1H, m), 4.41 (1H, br. s), 5.05 (1H, d, J=5.9), 5.41 (1H, d, J=4.9), 5.66 (1H, d, J=3.3), 8.07 (1H, br.s), 9.50 (1H, br.s )

Example 10

5'-deoxy-5-ethynyl-N$^4$-[(3-benzyloxypropoxy) carbonyl]cytidine

FAB-MS: (m/z) 444 [M+H]$^+$, $^1$H-NMR: (270 MHz; DMSO-d6): d 1.31 (3H, d, J=6.3), 1.90 (2H, tt, J=6.3, 6.3), 3.53 (2H, t, J=6.3), 3.69 (1H, m), 3.90 (1H, m), 4.09–4.19 (3H, m), 4.35 (1H, br.s), 4.47 (2H, s), 5.06 (1H, d, J=5.9), 5.42 (1H, d, J=5.0), 5.66 (1H, d, J=3.6), 7.27–7.38 (5H, m), 8.02 (1H, br.s), 9.50 (1H, br.s)

Example 11

5'-deoxy-5-ethynyl-N$^4$-[(2-methylthioethoxy) carbonyl]cytidine

FAB-MS: (m/z) 370 [M+H]$^+$, $^1$H-NMR: (270 MHz; CD3OD): d 1.51 (3H, d, J=6.3), 2.23 (3H, s), 2.88 (2H, t, J=6.9), 3.4 (1 H, m), 3.80 (1 H, m), 4.10–4.30 (2H, m), 4.42 (2H, m), 5.79 (1H, br.s), 8.22 (1H, br.s)

Example 12

5'-deoxy-5-ethynyl-N$^4$-[(2-ethylthioethoxy) carbonyl]cytidine

LC-MS: (m/z) 383.7 [M+H]$^+$, $^1$H-NMR: (270 MHz; DMSO-d6): d 1.19 (3H, t, J=6.6), 1.30 (3H, d, J=6.3), 2.58 (2H, q, J=6.6), 2.77 (2H, t, J=6.9), 3.68 (1H, m), 3.90 (1H, m), 4.10–4.20 (3H, m), 4.30 (1 H, br.s), 5.04 (1H, d, J=5.9), 5.39 (1H, d, J=5.0), 5.65 (1H, d, J=3.6), 7.97 (1H, s)

Example 13

5'-deoxy-5-ethynyl-N$^4$-[(2-phenylthioethoxy) carbonyl]cytidine

FAB-MS: (m/z) 432 [M+H]$^+$, $^1$H-NMR: (270 MHz; DMSO-d6): d 1.30 (3H, d, J=6.3), 3.27 (2H, t, J=6.5), 3.70 (1H, m), 3.90 (1H, m), 4.10–4.54 (4H, m), 5.05 (1H, d, J=5.7), 5.41 (1H, br.s), 5.66 (1H, br.d, J=3.3), 7.18–7.41 (5H, m), 7.91 (0.5H, br.s), 8.15 (0.5H, br.s), 9.50 (1H, br.s)

Example 14

5'-deoxy-5-ethynyl-N$^4$-[(3-methylthiopropoxy) carbonyl]cytidine

FAB-MS: (m/z) 384 [M+H]$^+$, $^1$ H-NMR: (270 MHz; DMSO-d6): d 1.31 (3H, d, J=6.3), 1.88 (2H, m), 2.05 (3H, s), 2.55 (2H, m), 3.71 (1H, m), 3.90 (1H, m), 4.13 (3H, m), 4.24 (0.5H, br.s), 4.46 (0.5H, br.s), 5.06 (1H, br.s), 5.40 (1H, br.s), 5.66 (1H, br.s), 7.89 (0.5H, br.s), 8.15 (0.5H, br.s), 9.53 (0.5H, br.s), 11.69 (0.5H, br.s)

Example 15

5'-deoxy-5-ethynyl-N$^4$-[(4-oxopentyloxy)carbonyl] cytidine

FAB-MS (m/z) 380 [M+H]$^+$, $^1$H-NMR: (270 MHz; DMSO-d6): d 1.31 (3H, br.s), 1.79 (2H, m), 2.10 (3H, s), 2.51–2.57 (2H, m), 3.70 (1H, m), 3.88–4.16 (4H, m), 4.23 (0.5H, br.s), 4.47 (0.5H, br.s), 5.04 (1H, br.s), 5.40 (1H, m), 5.67 (1H, br.s), 7.89 (0.5H, br.s), 8.15 (0.5H, br.s), 9.48 (0.5H, br.s), 11.68 (0.5H, br.s)

Example 16

5'-deoxy-5-ethynyl-N$^4$-[[2-(2-oxopyrrolidin-1-yl) ethoxy]carbonyl-cytidine

FAB-MS: (m/z) 407 [M+H]$^+$, $^1$H-NMR: (270 MHz; DMSO-d6): d 1.31 (3H, d, J=6.3), 1.92 (2H, m), 2.20 (2H, t, J=8.1), 3.42 (4H, m), 3.70 (1H, m), 3.91 (1H, m), 4.09 (1H, m), 4.16 (2H, m), 4.34 (1H, br.s), 5.07 (1H, d, J=5.9), 5.42 (1H, d, J =5.3), 5.66 (1H, d, J=3.6), 8.01 (1H, br.s)

Example 17

5'-deoxy-5-ethynyl-N$^4$-[(3-acetylaminopropoxy) carbonyl]cytidine

FAB-MS : (m/z) 395 [M+H]$^+$, $^1$H-NMR: (270 MHz; DMSO-d6): d 1.31 (3H, d, J=6.3), 1.74 (2H, m), 1.80 (3H, s), 3.11 (2H, m), 3.69 (1 H, m), 3.90 (1H, m), 4.08 (2H, m), 4.10 (1H, m) 4.36 (1H, br.s), 5.05 (1H, d, J=5.6), 5.40 (1H, d, J=4.3), 5.66 (1H, d, J=3.6), 7.88 (1H, m), 8.15 (1H br. s), 9.45 (1H, br.s)

Example 18

5'-deoxy-5-ethynyl-N$^4$-[(3-n-propionylaminopropoxy)-carbonyl]cytidine

FAB-MS: (m/z) 409 [M+H]$^+$, $^1$H-NMR: (270 MHz; DMSO-d6): d 0.99 (3H, t, J=7.6),1.30 (3H, d, J=6.3), 1.74 (2H, m), 2.06 (2H, q, J=7.6), 3.12 (2H, m), 3.70 (1H, m), 3.90 (1H, m), 4.07 (2H, m), 4.11 (1H, m), 4.34 (1H, br.s), 5.05 (1H, d, J=5.6), 5.40 (1H, d, J=5.3), 5.66 (1H, d, J=4.0), 7.80 (1H, m), 8.00 (1H, br.s)

Example 19

5'-deoxy-5-ethynyl-N$^4$-[(3-benzoylaminopropoxy) carbonyl]cytidine

FAB-MS: (mlz) 457 [M+H]$^+$, $^1$ H-NMR: (270 MHz; DMSO-d6): d 1.31 (3H, d, J=6.3), 1.89 (2H, m), 3.36 (2H, m), 3.69 (1H, m), 3.91 (1H, m), 4.12 (1H, m), 4.14 (2H, m), 4.34 (1H, br.s), 5.06 (1H, d, J=5.9), 5.41 (1H, d, J=5.0), 5.66 (1H, d, J=4.0), 7.48 (3H, m), 7.84 (2H, d, J=6.6), 8.00 (1H, br.s), 8.52 (1H, t, J=5.6), 9.45 (1H, br.s)

Example 20

5'-deoxy-5-ethynyl-N$^4$-[[2-(morpholin-4-yl)ethoxy] carbonyl]cytidine

FAB-MS: (m/z) 409 [M+H]$^+$, $^1$H-NMR: (270 MHz; DMSO-d6): d 1.31 (3H, d, J=6.3), 2.43 (4H, t, J=4.6), 2.58 (2H, t, J=5.8), 3.57 (4H, t, J=4.6), 3.69 (1H, m), 3.91 (1H, m), 4.14–4.21 (3H, m), 4.35 (1H, s), 5.06 (1H, br.s), 5.41 (1H, br.s), 5.66 (1H, d, J=4.0), 8.01 (1H, s)

Example 21

5'-deoxy-5-ethynyl-N$^4$-[(pyridin-3-ylmethoxy) carbonyl]cytidine

FAB-MS: (m/z) 387 [M+H]$^+$, $^1$H-NMR: (270 MHz; DMSO-d6): d 1.30 (3H, d, J=6.3), 3.68 (1H, m), 3.88 (1H, m), 4.11 (1H, m), 4.29 (1H, s), 5.04 (1H, d, J =5.6), 5.16 (2H, s), 5.39 (1H, d, J=5.0), 5.66 (1H, d, J=4.0), 7.42 (1H, dd, J=3.3, 7.6), 7.86 (1H, d, J=7.6), 7.96 (1 H, br.s), 8.55 (1H, d, J=3.3), 8.64 (1H, s)

Example 22

5'-deoxy-5-iodo-N$^4$-[(2,2-dimethyl-3-methoxypropoxy)-carbonyl]cytidine

FAB-MS: (m/z) 498 [M+H]$^+$, 520 [M+Na]$^+$, $^1$H-NMR: (270 MHz; DMSO-d6): d 0.90 (6H, s), 1.29 (3H, d, J=5.9), 3.12 (2H, s), 3.26 (3H, s), 3.66–3.72 (1H, m), 3.88–3.90

(3H, m), 4.16–4.21 (1H, m), 5.08 (1H, d, J=5.6), 5.38 (1H, d, J=5.3), 5.61 (1H, d, J=4.6), 7.99 (0.8H, br.s ), 8.17 (0.2H, br.s ), 9.46 (0.2H, br.s ), 11.76 (0.8H, br.s)

Example 23

5'-deoxy-$N^4$-[(2,2-dimethyl-3-methoxypropoxy)carbonyl]-5-vinylcytidine

FAB-MS: (m/z) 398 [M+H]⁺, 420 [M+Na]⁺, $^1$H-NMR: (400 MHz; DMSO-$d_6$): d 0.90 (6H, s), 1.32 (3H, d, J=5.9), 3.13 (2H, s), 3.25 (3H, s), 3.7–3.8 (1 H, m ), 3.87 (2H, s), 3.87–3.92 (1 H, m), 4.22 (1 H, m), 5.09 (1 H, d, J=4.4), 5.20–5.23 (1H, m), 5.41 (1H, d, J=4.4), 5.69 (1 H, d, J=4.4), 5.85–5.90 (1H, m), 6.59 (1H, dd, J=11, 17.6), 7.79 (1H, br.s), 7.95 (1H, br.s)

The following examples illustrate pharmaceutical preparations containing a compound provided by the present invention.

Example A

Interlocking gelatin capsules each containing the following ingredients were manufactured in a known manner:

| | |
|---|---|
| 5'-Deoxy-5-ethynyl-$N^4$-[(3-methoxy-2,2-dimethylpropoxy)carbonyl]cytidine | 40 mg |
| Lactose | 70 mg |
| Corn starch | 25 mg |
| Magnesium stearate | 1 mg |
| Crospovidone | 4 mg |
| | 140 mg |

Example B

Interlocking gelatin capsules each containing the following ingredients were manufactured in a known manner:

| | |
|---|---|
| 5'-Deoxy-fluoro-$N^4$-(n-pentyloxycarbonyl)cytidine | 100 mg |
| 5'-Deoxy-5-ethynyl-$N^4$-[(3-methoxy-2,2-dimethylpropoxy)carbonyl]cytidine | 10 mg |
| Lactose | 70 mg |
| Corn starch | 25 mg |
| Magnesium stearate | 1 mg |
| Crospovidone | 4 mg |
| | 210 mg |

Example C

Tablets each containing the following ingredients were manufactured in a known manner:

| | |
|---|---|
| 5'Deoxy-5-ethynyl-$N^4$-[(3-methoxy-2,2-dimethylpropoxy)carbonyl]cytidine | 40 mg |
| Lactose | 70 mg |
| Magnesium stearate | 3 mg |
| Crospovidone | 7 mg |
| Povidone | 10 mg |
| | 130 mg |

If necessary, the tablet can be film-coated with hydroxypropylmethyl cellulose, talc and colorant.

Example D

Tablets each containing the following ingredients were manufactured in a known manner:

| | |
|---|---|
| 5'-Deoxy-5-fluoro-$N^4$-(n-pentyloxycarbonyl)cytidine | 300 mg |
| 5'-Deoxy-5-ethynyl-$N^4$-[(3-methoxy-2,2-dimethylpropoxy)carbonyl]cytidine | 20 mg |
| Lactose | 70 mg |
| Magnesium stearate | 3 mg |
| Crospovidone | 7 mg |
| Povidone | 10 mg |
| | 186 mg |

If necessary, the tablet can be film-coated with hydroxypropylmethyl cellulose, talc and colorant.

We claim:

1. A compound of the formula (I),

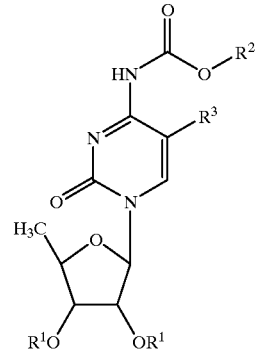

wherein $R^1$ is each independently hydrogen or a group easily hydrolyzable under physiological conditions;

$R^2$ is —(CH$_2$)$_n$-cycloalkyl wherein cycloalkyl contains 3 to 5 carbon atoms and n is an integer from 0 to 4, heteroaryl-(lower-alkyl), (lower-alkoxy)-(lower-alkyl), aryloxy-(lower-alkyl), aralkyloxy-(lower-alkyl), (lower-alkylthio)-(lower-alkyl), arylthio-(lower-alkyl), aralkylthio-(lower-alkyl), oxo-(lower-alkyl), acylamino-(lower-alkyl), cyclic amino-(lower-alkyl), (2-oxocyclic amino)-(lower-alkyl) wherein the alkylene chain is unsubstituted or substituted with one or two lower-alkyl group(s); and $R^3$ is iodo, or a vinyl or ethynyl group which vinyl or ethynyl group is unsubstituted or substituted with one or more substituents selected from the group consisting of halogen, $C_{1-4}$ alkyl, cycloalkyl, aralkyl, carbocyclic aromatic ring and heterocyclic aromatic ring.

2. A compound of claim 1, wherein $R^1$ is each independently hydrogen.

3. A compound of claim 2, wherein $R^2$ is —(CH$_2$)$_n$-cycloalkyl wherein cycloalkyl consists of 3 to 5 carbon atoms and n is an integer from 0 to 4.

4. A compound of claim 2, wherein $R^2$ is heteroaryl-(lower-alkyl).

5. A compound of claim 2, wherein $R^2$ is (lower-alkoxy)-(lower-alkyl).

6. A compound of claim 2, wherein $R^2$ is aryloxy-(lower-alkyl).

7. A compound of claim 2, wherein $R^2$ is (lower-alkylthio)-(lower-alkyl).

8. A compound of claim 2, wherein $R^2$ is arylthio-(lower-alkyl).

9. A compound of claim 2, wherein $R^2$ is aralkylthio-(lower-alkyl).

10. A compound of claim 2, wherein $R^2$ is oxo-(lower-alkyl).

11. A compound of claim 2, wherein $R^2$ is acylamino-(lower-alkyl).

12. A compound of claim 2, wherein $R^2$ is cyclic amino-(lower-alkyl).

13. A compound of claim 2, wherein $R^2$ is (2-oxocyclic amino)-(lower-alkyl) wherein the alkylene chain is unsubstituted or substituted with one or two lower-alkyl group(s).

14. A compound of claim 2, wherein $R^3$ is iodo.

15. A compound of claim 14, 5'-deoxy-5-iodo-$N^4$-[(2-methoxyethoxy) carbonyl]cytidine.

16. A compound of claim 14, 5'-deoxy-5-iodo-$N^4$-[(3-methoxy-3-methylbutoxy) carbonyl]-cytidine.

17. A compound of claim 14, 5'-deoxy-$N^4$-[(3-ethoxypropoxy)carbonyl]-5-iodocytidine.

18. A compound of claim 14, 5'-deoxy-5-iodo-$N^4$-[(3-methoxy-2,2-dimethylpropoxy)-carbonyl]cytidine.

19. A compound of claim 14, 5'-deoxy-$N^4$-[[2-ethyl-2-(methoxymethyl)butoxy]carbonyl]-5-iodocytidine.

20. A compound of claim 14, 5'-deoxy-$N^4$-[(3-benzyloxypropoxy)carbonyl]-5-iodocytidine.

21. A compound of claim 14, 5'-deoxy-$N^4$-(cyclobutoxycarbonyl)-5-iodocytidine.

22. A compound of claim 14, 5'-deoxy-$N^4$-[(cyclopropylmethoxy)carbonyl]-5-iodocytidine.

23. A compound of claim 14, 5'-deoxy-$N^4$-[(cyclobutylmethoxy)carbonyl]-5-iodocytidine.

24. A compound of claim 14, 5'-deoxy-$N^4$-[(cyclopentylmethoxy)carbonyl]-5-iodocytidine.

25. A compound of claim 14, 5'-deoxy-$N^4$-[(2-methylthioethoxy)carbonyl]-5-iodocytidine.

26. A compound of claim 14, 5'-deoxy-5-iodo-$N^4$-[(2-ethylthioethoxy)carbonyl]cytidine.

27. A compound of claim 14, 5'-deoxy-$N^4$-[(2-phenylthioethoxy)carbonyl]-5-iodocytidine.

28. A compound of claim 14, 5'-deoxy-5-iodo-$N^4$-[(2-methylthiopropoxy)carbonyl]cytidine.

29. A compound of claim 14, 5'-deoxy-5-iodo-$N^4$-[(4-oxopentyloxy)carbonyl]cytidine.

30. A compound of claim 14, 5'-deoxy-5-iodo-$N^4$-[[2-(2-oxopyrrolidin-1-yl)ethoxy]-carbonyl]cytidine.

31. A compound of claim 14, $N^4$-[[3-(acetylamino)propoxy]carbonyl]-5'-deoxy-5-iodocytidine.

32. A compound of claim 14, 5'-deoxy-5-iodo-$N^4$-[[3-(n-propionylamino)propoxy]-carbonyl]cytidine.

33. A compound of claim 14, 5'-deoxy-5-iodo-$N^4$-[(2-morpholinoethoxy)carbonyl]cytidine.

34. A compound of claim 14, 5'-deoxy-5-iodo-$N^4$-[(pyridin-3-ylmethoxy)carbonyl]cytidine.

35. A compound of claim 14, 2',3'-di-O-acetyl-5'-deoxy-5-iodo-$N^4$-[(3-methoxy-3-methylbutoxy)carbonyl]cytidine.

36. A compound of claim 2, wherein $R^3$ is a vinyl which is unsubstituted or substituted with one or more substituents selected from the group consisting of halogen, $C_{1-4}$ alkyl, cycloalkyl, aralkyl, carbocyclic aromatic ring and heterocyclic aromatic ring.

37. A compound of claim 36, 5'-deoxy-$N^4$-[(2-methoxyethoxy)carbonyl]-5-vinylcytidine.

38. A compound of claim 36, 5'-deoxy-$N^4$-[(3-methoxy-3-methylbutoxy)carbonyl]-5-vinyl-cytidine.

39. A compound of claim 36, 5'-deoxy-$N^4$-[(3-ethoxypropoxy)carbonyl]-5-vinylcytidine.

40. A compound of claim 36, 5'-deoxy-$N^4$-[(3-methoxy-2,2-dimethylpropoxy)carbonyl]-5-vinylcytidine.

41. A compound of claim 36, 5'-deoxy-$N^4$-[[2-ethyl-2-(methoxymethyl)butoxy]carbonyl]-5-vinylcytidine.

42. A compound of claim 36, $N^4$-[(3-benzyloxypropoxy)carbonyl]-5'-deoxy-5-vinylcytidine.

43. A compound of claim 36, $N^4$-(cyclobutoxycarbonyl)-5'-deoxy-5-vinylcytidine.

44. A compound of claim 36, $N^4$-[(cyclopropylmethoxy)carbonyl]-5'-deoxy-5-vinylcytidine.

45. A compound of claim 36, $N^4$-[(cyclobutylmethoxy)carbonyl]-5'-deoxy-5-vinylcytidine.

46. A compound of claim 36, $N^4$-[(cyclopentylmethoxy)carbonyl]-5'-deoxy-5-vinylcytidine.

47. A compound of claim 36, 5'-deoxy-$N^4$-[(2-methylthioethoxy)carbonyl]-5-vinylcytidine.

48. A compound of claim 36, 5'-deoxy-$N^4$-[(2-ethylthioethoxy)carbonyl]-5-vinylcytidine.

49. A compound of claim 36, 5'-deoxy-$N^4$-[(2-phenylthioethoxy)carbonyl]-5-vinylcytidine.

50. A compound of claim 36, 5'-deoxy-$N^4$-[(2-methylthiopropoxy)carbonyl]-5-vinylcytidine.

51. A compound of claim 36, 5'-deoxy-$N^4$-[(4-oxopentyloxy)carbonyl]-5-vinylcytidine.

52. A compound of claim 36, 5'-deoxy-$N^4$-[[2-(2-oxopyrrolidin-1-yl)ethoxy]carbonyl]-5-vinylcytidine.

53. A compound of claim 36, $N^4$-[[3-(acetylamino)propoxy]carbonyl]-5'-deoxy-5-vinylcytidine.

54. A compound of claim 36, 5'-deoxy-$N^4$-[[3-(n-propionylamino)propoxy]-5-vinylcytidine.

55. A compound of claim 36, 5'-deoxy-$N^4$-[(2-morpholinoethoxy)carbonyl]-5-vinylcytidine.

56. A compound of claim 36, 5'-deoxy-$N^4$-[(pyridin-3-ylmethoxy)carbonyl]-5-vinylcytidine.

57. A compound of claim 36, 2',3'-di-O-acetyl-5'-deoxy-$N^4$-[(3-methoxy-3-methylbutoxy)carbonyl]-5-vinylcytidine.

58. A compound of claim 2, wherein $R^3$ is a ethynyl which is unsubstituted or substituted with one or more substituents selected from the group consisting of halogen, $C_{1-4}$ alkyl, cycloalkyl, aralkyl, carbocyclic aromatic ring and heterocyclic aromatic ring.

59. A compound of claim 58, 5'-deoxy-5-ethynyl-$N^4$-[(2-methoxyethoxy)carbonyl]cytidine.

60. A compound of claim 58, 5'-deoxy-5-ethynyl-$N^4$-[(3-methoxy-3-methylbutoxy)carbonyl]-cytidine.

61. A compound of claim 58, 5'-deoxy-5-ethynyl-$N^4$-[(3-ethoxypropoxy)carbonyl]cytidine.

62. A compound of claim 58, 5'-deoxy-5-ethynyl-$N^4$-[(3-methoxy-2,2-dimethylpropoxy)-carbonyl]cytidine.

63. A compound of claim 58, 5'-deoxy-5-ethynyl-$N^4$-[[2-ethyl-2-(methoxymethyl)butoxy]-carbonyl]cytidine.

64. A compound of claim 58, 5'-deoxy-5-ethynyl-$N^4$-[(3-benzyloxypropoxy)carbonyl]cytidine.

65. A compound of claim 58, 5'-deoxy-5-ethynyl-$N^4$-(cyclobutoxycarbonyl)cytidine.

66. A compound of claim 58, 5'-deoxy-5-ethynyl-$N^4$-[(cyclopropylmethoxy)carbonyl]cytidine.

67. A compound of claim 58, 5'-deoxy-5-ethynyl-$N^4$-[(cyclobutylmethoxy)carbonyl]cytidine.

68. A compound of claim 58, 5'-deoxy-5-ethynyl-$N^4$-[(cyclopentylmethoxy)carbonyl]cytidine.

69. A compound of claim 58, 5'-deoxy-5-ethynyl-$N^4$-[(2-methylthioethoxy)carbonyl]cytidine.

70. A compound of claim 58, 5'-deoxy-5-ethynyl-$N^4$-[(2-ethylthioethoxy)carbonyl]cytidine.

71. A compound of claim 58, 5'-deoxy-5-ethynyl-$N^4$[(2-phenylthioethoxy)carbonyl]cytidine.

72. A compound of claim 58, 5'-deoxy-5-ethynyl-$N^4$-[(2-methylthiopropoxy)carbonyl]cytidine.

73. A compouond of claim 58, 5'-deoxy-5-ethynyl-$N^4$-[(4-oxopentyloxy)carbonyl]cytidine.

74. A compound of claim 58, 5'-deoxy-5-ethynyl-$N^4$-[[2-(2-oxopyrrolidin-1-yl)ethoxy]-carbonyl]cytidine.

75. A compound of claim 58, 5'-deoxy-5-ethynyl-$N^4$-[[3-(acetylamino)propoxy]carbonyl]-cytidine.

76. A compound of claim 58, 5'-deoxy-5-ethynyl-$N^4$-[[3-(n-propionylamino)propoxy]-carbonyl]cytidine.

77. A compound of claim 58, 5'-deoxy-5-ethynyl-$N^4$-[(2-morpholinoethoxy)carbonyl]cytidine.

78. A compound of claim 58, 5'-deoxy-5-ethynyl-$N^4$-[(pyridin-3-ylmethoxy)carbonyl]cytidine.

79. A compound of claim 58, 2',3'-di-O-acetyl-5'-deoxy-5-ethynyl-$N^4$-[(3-methoxy-3-methylbutoxy)carbonyl]cytidine.

* * * * *

UNITED STATES PATENT AND TRADEMARK OFFICE
CERTIFICATE OF CORRECTION

PATENT NO. : 6,005,098
DATED : December 21, 1998
INVENTOR(S) : Hattori, et al.

It is certified that error appears in the above-identified patent and that said Letters Patent is hereby corrected as shown below:

Claim 73, Column 21, line 9: "compouond" should read --- compound ---.

Signed and Sealed this

Twenty-ninth Day of August, 2000

Attest:

Q. TODD DICKINSON

*Attesting Officer*  *Director of Patents and Trademarks*